US012778421B2

(12) United States Patent
Tsai et al.

(10) Patent No.: US 12,778,421 B2
(45) Date of Patent: Nov. 3, 2026

(54) OPTICAL DETECTION SYSTEM INTEGRATING TONOMETER AND AUTOREFRACTOR

(71) Applicant: Crystalvue Medical Corporation, Taoyuan City (TW)

(72) Inventors: Che-Liang Tsai, Taoyuan City (TW); Yen-Jen Chang, Taoyuan City (TW); Chung-Ping Chuang, Taoyuan City (TW); Tung-Yu Lee, Taoyuan City (TW); Sung-Yang Wei, Taoyuan City (TW); William Wang, Taoyuan City (TW)

(73) Assignee: Crystalvue Medical Corporation, Taoyuan City (TW)

( * ) Notice: Subject to any disclaimer, the term of this patent is extended or adjusted under 35 U.S.C. 154(b) by 219 days.

(21) Appl. No.: 18/794,185

(22) Filed: Aug. 5, 2024

(65) Prior Publication Data

US 2025/0049319 A1 Feb. 13, 2025

Related U.S. Application Data

(60) Provisional application No. 63/531,578, filed on Aug. 9, 2023.

(51) Int. Cl.
*A61B 3/18* (2006.01)
*A61B 3/103* (2006.01)
*A61B 3/16* (2006.01)

(52) U.S. Cl.
CPC ................ *A61B 3/18* (2013.01); *A61B 3/103* (2013.01); *A61B 3/165* (2013.01)

(58) Field of Classification Search
CPC ........... A61B 3/18; A61B 3/103; A61B 3/165; A61B 3/16
USPC ........................................................ 351/205
See application file for complete search history.

(56) References Cited

U.S. PATENT DOCUMENTS 7,123,751 B1 * 10/2006 Fujieda .................. A61B 3/107 340/5.83
2017/0065174 A1 * 3/2017 Yamamoto ............. A61B 3/103

* cited by examiner

*Primary Examiner* — Travis S Fissel
(74) *Attorney, Agent, or Firm* — Patterson + Sheridan, LLP

(57) ABSTRACT

An optical detection system integrating tonometer and autorefractor includes first and second optical modules. The first optical module includes a light source, first and second lens sets, a reflector, a first light-splitter and a sensor. The first lens set and reflector are disposed corresponding to light source. The first light-splitter is disposed corresponding to the reflector, second lens set and sensor. The second optical module includes a second light-splitter and first to third optical elements. The incident light emitted by the light source passes through the first lens, reflected by the reflector, passes through the first light-splitter, reflected by the second light-splitter, passes through the first to third optical elements and emitted to an eye. A sensing light from the eye passes through the third to first optical elements, reflected by the second light-splitter and first light-splitter, passes through the second lens set and emitted to the sensor.

11 Claims, 3 Drawing Sheets

OPTICAL DETECTION SYSTEM INTEGRATING TONOMETER AND AUTOREFRACTOR

CROSS REFERENCE TO RELATED APPLICATIONS

This Application is a non-provisional application claiming priority to U.S. Provisional Application 63/531,578, filed on Aug. 9, 2023, which is incorporated by reference in its entirety.

BACKGROUND OF THE INVENTION

Field of the Invention

The invention relates to optical detection; in particular, to an optical detection system integrating tonometer and autorefractor.

Description of the Prior Art

Figure 1:
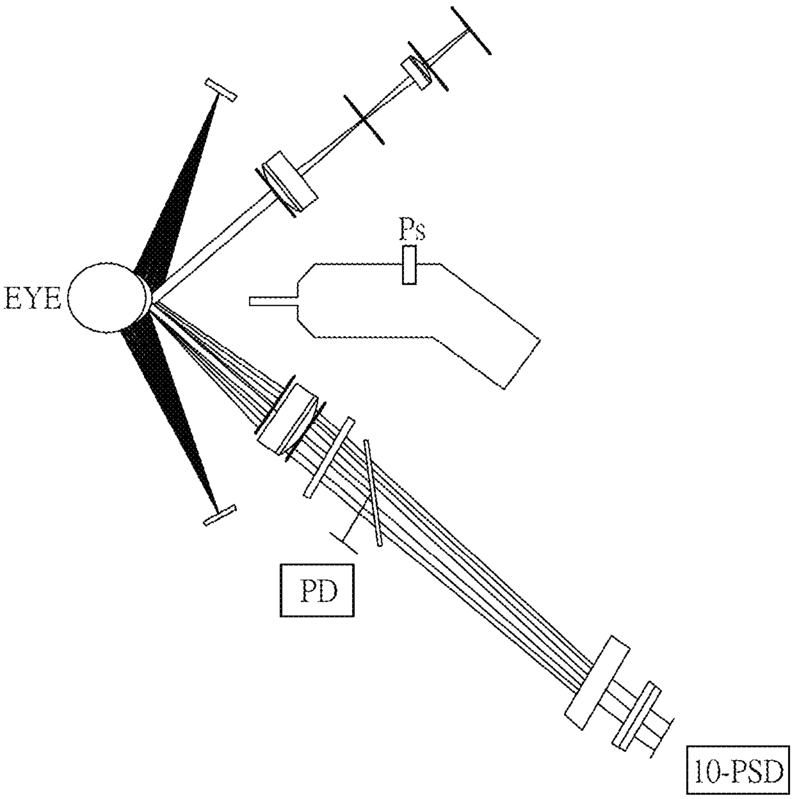
FIG. 1 (PRIOR ART)
Figure 2:
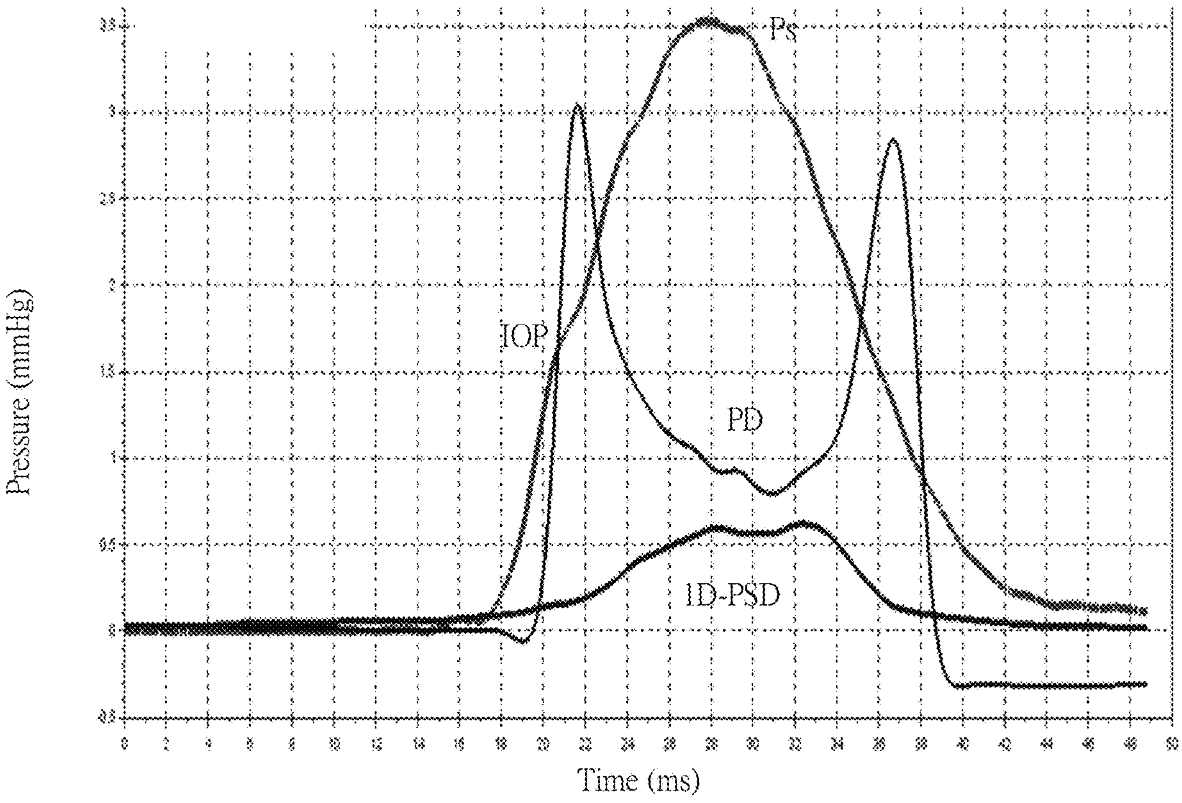
FIG. 2 (PRIOR ART)

Please refer to FIG. 1 and FIG. 2. FIG. 1 and FIG. 2 respectively illustrate a schematic diagram of intraocular pressure measurement of the eye through a conventional tonometer and a graph of pressure changes over time, where Ps is a pressure sensor in the system; PD is a monitor used to monitor the flatness (applanation status) of the cornea of the eye EYE; 1D-PSD is a monitor used to monitor the position of the cornea of the eye EYE; IOP is the measured intraocular pressure.

However, the conventional tonometer is still unable to be integrated with autorefractors and other optical equipment into a multi-functional optical detection system and need to be further improved.

SUMMARY OF THE INVENTION

Therefore, the invention provides an optical detection system integrating tonometer and autorefractor to solve the above-mentioned problems of the prior arts.

A preferred embodiment of the invention is an optical detection system integrating tonometer and autorefractor. In this embodiment, the optical detection system includes a first optical module and a second optical module. The first optical module includes a light source, a first lens set, a second lens set, a reflector, a first light-splitter and a sensor, wherein the first lens set and the reflector are disposed corresponding to the light source, and the first light-splitter is disposed corresponding to the reflector, the second lens set and the sensor. The second optical module includes a second light-splitter and a first optical element, a second optical element and a third optical element. The incident light emitted by the light source passes through the first lens, reflected by the reflector, passes through the first light-splitter, reflected by the second light-splitter, passes through the first optical element, the second optical element and the third optical element, and then emitted to an eye. A sensing light from the eye passes through the third optical element, the second optical element and the first optical element, reflected by the second light-splitter and the first light-splitter, passes through the second lens set and then emitted to the sensor.

In an embodiment, the first optical module includes an autorefractor.

In an embodiment, the second optical module includes a tonometer.

In an embodiment, there is air entering between the first optical element and the second optical element of the second optical module.

In an embodiment, the first optical module further includes a pinhole, and the pinhole is disposed between the first light-splitter and the second lens set. The sensing light reflected by the first light-splitter passes through the pinhole and then pass through the second lens set.

In an embodiment, the second optical module further includes a third light-splitter, a filter, a third lens set and a second sensor. The third light-splitter is disposed relative to the second light-splitter. The second sensor is disposed on the other side away from the eye. The filter and the third lens set are sequentially disposed between the third light-splitter and the second sensor.

In an embodiment, an image from outside the eye passes through the third optical element, the second optical element, the first optical element, the second light-splitter, the third light-splitter, the filter, and the third lens set sequentially to the second sensor to form a video path.

In an embodiment, the optical detection system further includes a third optical module configured to provide Scheimpflug optical path, wherein the third optical module includes a fourth lens set, a slit, a fifth lens set, a fourth light-splitter and a fifth light-splitter. The slit is disposed between the fourth lens set and the fifth lens set. The fifth light-splitter is disposed corresponding to the first light-splitter and the second light-splitter, and the fourth light-splitter is disposed between the fifth light-splitter and the fifth lens set.

In an embodiment, the Scheimpflug optical path is formed by sequentially passing through the fourth lens set, the slit, the fifth lens set and the fourth light-splitter, and then being reflected by the fifth light-splitter into the second optical module and being reflected by the second optical module, and then passing through the first optical element, the second optical element and the third optical element in sequence and then being emitted to the eye.

In an embodiment, the optical detection system further includes a fourth optical module including a second reflector, a sixth lens set and a fixed end, wherein the second reflector is disposed corresponding to the fourth light-splitter. The sixth lens set is disposed between the second reflector and the fixed end. The fixed end moves horizontally to be close to or away from the sixth lens set, thereby an optical path difference from the fixed end through the sixth lens set and reflected by the second reflector to the fourth light-splitter of the third optical module is generated.

In an embodiment, the optical detection system further includes a fifth optical module including a third reflector, a sixth light-splitter and a seventh lens set. The third reflector is disposed corresponding to the third light-splitter, and the sixth light-splitter is disposed corresponding to the third reflector. The seventh lens set is disposed corresponding to the sixth light-splitter.

In an embodiment, a XY axis alignment path is formed by passing through the seventh lens set and being sequentially reflected by the sixth light-splitter and the third reflector to the third light-splitter of the second optical module.

In an embodiment, a K1/K2 path is formed by passing through the sixth light-splitter and being reflected by the third reflector to the third light-splitter of the second optical module.

Compared to the prior art, the optical detection system proposed by the invention can simultaneously integrate tonometer and autorefractor into the same system through the design of multiple optical modules, and can also provide a video path, a Scheimpflug optical path, XY axis alignment path and other optical paths to achieve an integrated multi-functional optical inspection system.

The advantage and spirit of the invention may be understood by the following detailed descriptions together with the appended drawings.

BRIEF DESCRIPTION OF THE APPENDED DRAWINGS

Figure 3:
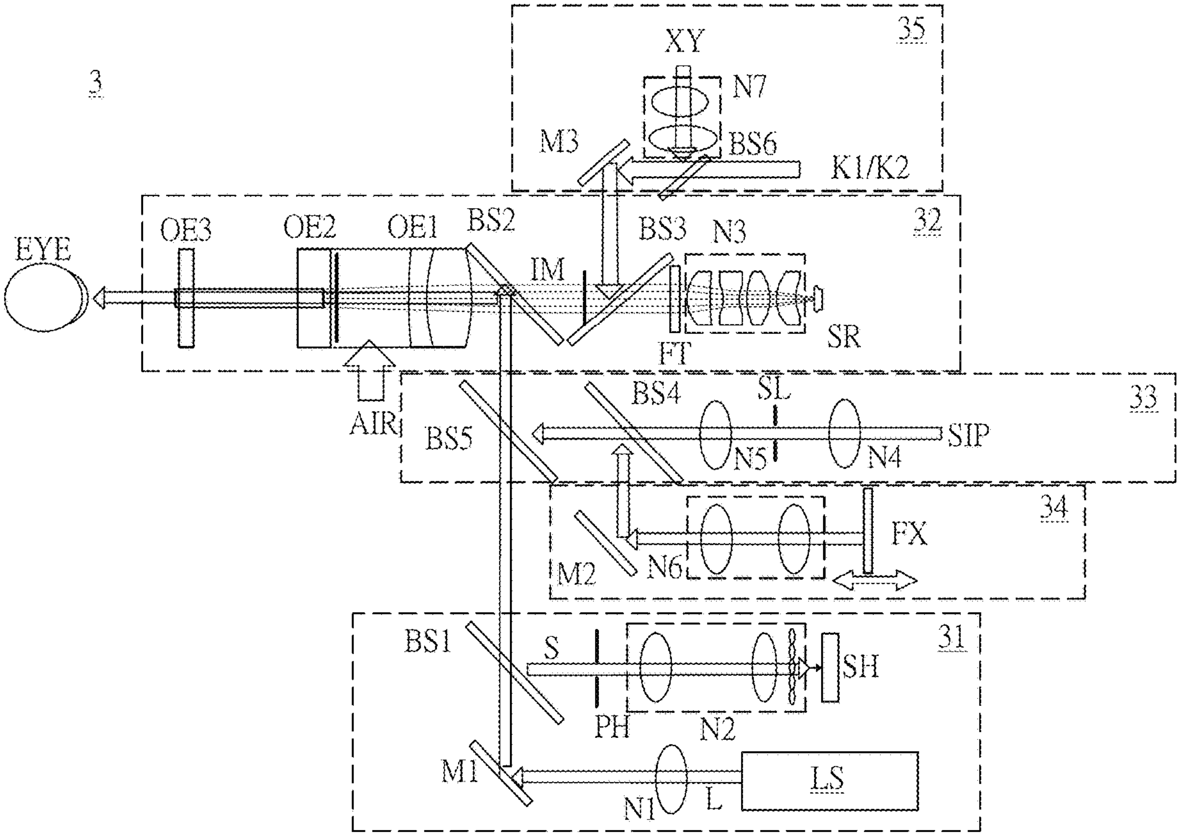

FIG. 1 and FIG. 2 respectively illustrate a schematic diagram of intraocular pressure measurement of the eye through a conventional tonometer and a graph of pressure changes over time FIG. 3 illustrates a schematic diagram of an optical detection system integrating tonometer and autorefractor in an embodiment of the invention.

DETAILED DESCRIPTION OF THE INVENTION

Reference will now be made in detail to the exemplary embodiments of the present invention, examples of which are illustrated in the accompanying drawings. Elements/components with the same or similar numbers used in the drawings and embodiments are intended to represent the same or similar parts.

A specific embodiment of the invention is an optical detection system integrating tonometer and autorefractor. The tonometer and autorefractor can be integrated into the same system through the design of multiple optical modules. And, this optical detection system can be implemented as a single optical detection device or a combination of multiple optical detection devices, without specific limitations.

In this embodiment, the optical detection system 3 includes a first optical module 31, a second optical module 32, a third optical module 33, a fourth optical module 34 and a fifth optical module 35. The first optical module 31 includes an autorefractor and the second optical module 32 includes a tonometer.

The first optical module 31 includes a light source LS, a first lens set N1, a second lens set N2, a first reflector M1, a first light-splitter BS1, a pinhole PH and a first sensor SH. The first lens set N1 and the first reflector M1 are disposed corresponding to the light source LS. The first light-splitter BS1 is disposed corresponding to the first reflector M1, the pinhole PH, the second lens set N2 and the first sensor SH. In practical applications, the light source LS can be a laser light source, the first lens set N1 can include a single lenticular lens, and the second lens set N2 can include two lenticular lenses and a microlens array, but not limited to this.

The second optical module 32 includes a second light-splitter BS2, a third light-splitter BS3, a first optical element OE1, a second optical element OE2, a third optical element OE3, a filter FT, a third lens set N3 and a second sensor SR. The second light-splitter BS2, the first optical element OE1, the second optical element OE2 and the third optical element OE3 are disposed corresponding to each other in sequence. The third optical element OE3 is disposed on a side close to the eye EYE. Air AIR will enter between the first optical element OE1 and the second optical element OE2. The third light-splitter BS3 is disposed relative to the second light-splitter BS2. The second sensor SR is disposed on the other side away from the eye EYE. The filter FT and the third lens set N3 are sequentially disposed between the third light-splitter BS3 and the second sensor SR.

In practical applications, the first optical element OE1 can include a focusing lens to focus the light to the second optical element OE2; the filter FT is used to filter the light to filter out lights of specific wavelengths; the third lens set N3 can include a combination of multiple different types of lenses, such as a combination of convex plano lenses, biconcave lenses, biconvex lenses, and convex-concave lenses, but not limited to this.

When the light source LS of the first optical module 31 emits an incident light L, the incident light L sequentially passes through the first lens set N1, is reflected by the first reflector M1, passes through the first light-splitter BS1 and is then emitted out of the first optical module 31. Then, after the incident light L enters the second optical module 32, the incident light L is reflected by the second light-splitter BS2 in sequence, passes through the first optical element OE1, the second optical element OE2 and the third optical element OE3 in sequence, and is then emitted to the eye EYE.

When the incident light L is emitted to the eye EYE, the eye EYE reflects the incident light L to form a sensing light S entering the second optical module 32. The sensing light S sequentially passes through the third optical element OE3, the second optical element OE2 and the first optical element OE1 in the second optical module 32, is reflected by the second light-splitter BS2, and then exits the second optical module 32. Next, when the sensing light S is emitted to the first optical module 31, the sensing light S is reflected by the first light-splitter BS1, passes through the pinhole PH and the second lens set N2, and is then emitted to the first sensor SH.

In addition, in the second optical module 32, the image IM from the outer part of the eye EYE (such as the iris) sequentially passes through the third optical element OE3, the second optical element OE2, the first optical element OE1, the second light-splitter BS2, the third light-splitter BS3, the filter FT and the third lens set N3 and is then emitted to the second sensor SR to form a video path.

The third optical module 33 includes a fourth lens set N4, a slit SL, a fifth lens set N5, a fourth light-splitter BS4 and a fifth light-splitter BS5. The slit SL is disposed between the fourth lens set N4 and the fifth lens set N5. The second light-splitter BS5 is disposed corresponding to the first light-splitter BS1 and the second light-splitter BS2. The fourth light-splitter BS4 is disposed between the fifth light-splitter BS5 and the fifth lens set N5. In practical applications, the fourth lens set N4 can include a single lenticular lens, and the fifth lens set N5 can include a single lenticular lens, but not limited to this.

The third optical module 33 is used to provide Scheimpflug optical path SIP. The Scheimpflug optical path SIP is formed by sequentially passing through the fourth lens set N4, the slit SL, the fifth lens set N5 and the fourth light-splitter BS4, and then being reflected by the fifth light-splitter BS5 into the second optical module 32, and then being reflected by the second light-splitter BS2, and then passing through the first optical element OE1, the second optical element OE2 and the third optical element OE3 in sequence and then being emitted to the eye EYE.

The fourth optical module 34 includes a second reflector M2, a sixth lens set N6 and a fixed end FX. The second reflector M2 is disposed corresponding to the fourth light-splitter BS4. The sixth lens set N6 is disposed between the second reflector M2 and the fixed end FX. The fixed end FX can move horizontally to be closer to or away from the sixth lens set N6, thereby an optical path difference from the fixed end FX through the sixth lens set N6 and reflected by the second reflector M2 to the fourth light-splitter BS4 of the third optical module 33 is generated. In practical applications, the sixth lens set N6 can include two biconvex lenses, but not limited to this.

The fifth optical module 35 includes a third reflector M3, a sixth light-splitter BS6 and a seventh lens set N7. The third reflector M3 is disposed corresponding to the third light-splitter BS3. The sixth light-splitter BS6 is disposed corresponding to the third reflector M3. The seventh lens set N7 is disposed corresponding to the sixth light-splitter BS6. In practical applications, the seventh lens set N7 can include two biconvex lenses, but not limited to this.

The XY axis alignment path XY is formed by passing through the seventh lens set N7 and being sequentially reflected by the sixth light-splitter BS6 and the third reflector M3 to the third light-splitter BS3 of the second optical module 32. The K1/K2 path K1/K2 is formed by passing through the sixth light-splitter BS6 and being reflected by the third reflector M3 to the third light-splitter BS3 of the second optical module 32.

Compared to the prior art, the optical detection system proposed by the invention can simultaneously integrate tonometer and autorefractor into the same system through the design of multiple optical modules, and can also provide a video path, a Scheimpflug optical path, XY axis alignment path and other optical paths to achieve an integrated multi-functional optical inspection system.

With the example and explanations above, the features and spirits of the invention will be hopefully well described. Those skilled in the art will readily observe that numerous modifications and alterations of the device may be made while retaining the teaching of the invention. Accordingly, the above disclosure should be construed as limited only by the metes and bounds of the appended claims.

What is claimed is:

1. An optical detection system integrating tonometer and autorefractor, comprising:

a first optical module comprising a light source, a first lens set, a second lens set, a reflector, a first light-splitter and a sensor, wherein the first lens set and the reflector are disposed corresponding to the light source, and the first light-splitter is disposed corresponding to the reflector, the second lens set and the sensor; and a second optical module comprising a second light-splitter and a first optical element, a second optical element and a third optical element;

wherein a light emitted by the light source passes through the first lens set, reflected by the reflector, passes through the first light-splitter, reflected by the second light-splitter, passes through the first optical element, the second optical element and the third optical element, and then emitted to an eye; a sensing light from the eye passes through the third optical element, the second optical element and the first optical element, reflected by the second light-splitter and the first light-splitter, passes through the second lens set and then emitted to the sensor; the first optical module further comprises a pinhole, and the pinhole is disposed between the first light-splitter and the second lens set; the sensing light reflected by the first light-splitter passes through the pinhole and then passes through the second lens set.

2. The optical detection system of claim 1, wherein the first optical module comprises an autorefractor.

3. The optical detection system of claim 1, wherein the second optical module comprises a tonometer.

4. The optical detection system of claim 1, wherein there is air entering between the first optical element and the second optical element of the second optical module.

5. An optical detection system integrating tonometer and autorefractor, comprising:

a first optical module comprising a light source, a first lens set, a second lens set, a reflector, a first light-splitter and a sensor, wherein the first lens set and the reflector are disposed corresponding to the light source, and the first light-splitter is disposed corresponding to the reflector, the second lens set and the sensor; and a second optical module comprising a second light-splitter and a first optical element, a second optical element and a third optical element;

wherein a light emitted by the light source passes through the first lens set, reflected by the reflector, passes through the first light-splitter, reflected by the second light-splitter, passes through the first optical element, the second optical element and the third optical element, and then emitted to an eye; a sensing light from the eye passes through the third optical element, the second optical element and the first optical element, reflected by the second light-splitter and the first light-splitter, passes through the second lens set and then emitted to the sensor; the second optical module further comprises a third light-splitter, a filter, a third lens set and a second sensor; the third light-splitter is disposed relative to the second light-splitter, the second sensor is disposed on the other side away from the eye, the filter and the third lens set are sequentially disposed between the third light-splitter and the second sensor; an image from outside the eye passes through the third optical element, the second optical element, the first optical element, the second light-splitter, the third light-splitter, the filter, and the third lens set sequentially to the second sensor to form a video path.

6. An optical detection system integrating tonometer and autorefractor, comprising:

a first optical module comprising a light source, a first lens set, a second lens set, a reflector, a first light-splitter and a sensor, wherein the first lens set and the reflector are disposed corresponding to the light source, and the first light-splitter is disposed corresponding to the reflector, the second lens set and the sensor;

a second optical module comprising a second light-splitter and a first optical element, a second optical element and a third optical element; and a third optical module configured to provide Scheimpflug optical path, wherein the third optical module comprises a fourth lens set, a slit, a fifth lens set, a fourth light-splitter and a fifth light-splitter, the slit is disposed between the fourth lens set and the fifth lens set, the fifth light-splitter is disposed corresponding to the first light-splitter and the second light-splitter, and the fourth light-splitter is disposed between the fifth light-splitter and the fifth lens set;

wherein a light emitted by the light source passes through the first lens set, reflected by the reflector, passes through the first light-splitter, reflected by the second light-splitter, passes through the first optical element, the second optical element and the third optical element, and then emitted to an eye; a sensing light from the eye passes through the third optical element, the second optical element and the first optical element, reflected by the second light-splitter and the first light-splitter, passes through the second lens set and then emitted to the sensor.

7. The optical detection system of claim 6, wherein the Scheimpflug optical path is formed by sequentially passing through the fourth lens set, the slit, the fifth lens set and the fourth light-splitter, and then being reflected by the fifth light-splitter into the second optical module and being reflected by the second optical module, and then passing through the first optical element, the second optical element and the third optical element in sequence and then being emitted to the eye.

8. The optical detection system of claim 6, further comprising:

a fourth optical module comprising a second reflector, a sixth lens set and a fixed end, wherein the second reflector is disposed corresponding to the fourth light-splitter, the sixth lens set is disposed between the second reflector and the fixed end, the fixed end moves horizontally to be close to or away from the sixth lens set, thereby an optical path difference from the fixed end through the sixth lens set and reflected by the second reflector to the fourth light-splitter of the third optical module is generated.

9. The optical detection system of claim 8, further comprising:

a fifth optical module comprising a third reflector, a sixth light-splitter and a seventh lens set, the third reflector is disposed corresponding to the third light-splitter, and the sixth light-splitter is disposed corresponding to the third reflector, the seventh lens set is disposed corresponding to the sixth light-splitter.

10. The optical detection system of claim 9, wherein a XY axis alignment path is formed by passing through the seventh lens set and being sequentially reflected by the sixth light-splitter and the third reflector to the third light-splitter of the second optical module.

11. The optical detection system of claim 9, wherein a K1/K2 path is formed by passing through the sixth light-splitter and being reflected by the third reflector to the third light-splitter of the second optical module.

* * * * *